(12) United States Patent
Ochi et al.

(10) Patent No.: US 11,187,667 B2
(45) Date of Patent: Nov. 30, 2021

(54) BIOLOGICAL SAMPLE MEASURING APPARATUS

(71) Applicant: PHC Holdings Corporation, Tokyo (JP)

(72) Inventors: Hirotaka Ochi, Ehime (JP); Keisuke Matsumura, Ehime (JP); Hitoshi Fujino, Ehime (JP); Yohei Hashimoto, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 0 days.

(21) Appl. No.: 15/787,634

(22) Filed: Oct. 18, 2017

(65) Prior Publication Data

US 2018/0067072 A1    Mar. 8, 2018

Related U.S. Application Data

(63) Continuation of application No. 14/354,132, filed as application No. PCT/JP2012/006762 on Oct. 23, 2012, now Pat. No. 9,823,214.

(30) Foreign Application Priority Data

Nov. 1, 2011  (JP) ................................. 2011-239996
Nov. 1, 2011  (JP) ................................. 2011-239997

(51) Int. Cl.
*G01N 27/327*    (2006.01)
*G01K 7/42*       (2006.01)
(Continued)

(52) U.S. Cl.
CPC ............ *G01N 27/3274* (2013.01); *A61B 5/00* (2013.01); *A61B 5/01* (2013.01); *A61B 5/145* (2013.01);
(Continued)

(58) Field of Classification Search
None
See application file for complete search history.

(56) References Cited

U.S. PATENT DOCUMENTS 5,366,609 A * 11/1994 White ............... G01N 33/48792
                                              204/403.04
5,405,511 A *  4/1995 White ...................... G01K 7/42
                                              204/403.04

(Continued)

FOREIGN PATENT DOCUMENTS

JP    H03-075530 A    3/1991
JP    H07-008393 A    1/1995
(Continued)

OTHER PUBLICATIONS

The International Search Report of Int'l Appl. No. PCT/JP2012/006762 dated Nov. 27, 2012.
(Continued)

*Primary Examiner* — Catherine T. Rastovski
*Assistant Examiner* — Leonard S Liang
(74) *Attorney, Agent, or Firm* — Wenderoth, Lind & Ponack, L.L.P.

(57) ABSTRACT

The present invention includes a body case having a biological sample sensor mounting portion on one end side, a temperature sensor (A) provided on the one end side inside the body case, a measurement portion connected to the biological sample sensor mounting portion, and a control portion connected to the measurement portion. A temperature sensor (B) is provided on one other end side inside the body case, and when measurement is performed by the measurement portion, temperature change amounts in the two end portions are compared using the temperature sensors (A) and (B). Furthermore, a measurement value obtained by the measurement portion is corrected using temperature information from either one of the temperature (Continued)

sensors (A) or (B) that is provided in the end portion on the side where the temperature change is smaller.

6 Claims, 12 Drawing Sheets

(51) Int. Cl.

| | | |
|---|---|---|
| G01D 9/00 | | (2006.01) |
| G01D 3/02 | | (2006.01) |
| G16B 20/00 | | (2019.01) |
| G01N 33/66 | | (2006.01) |
| A61B 5/01 | | (2006.01) |
| A61B 5/145 | | (2006.01) |
| A61B 5/00 | | (2006.01) |
| G01N 33/487 | | (2006.01) |
| G01N 33/50 | | (2006.01) |

(52) U.S. Cl.
CPC .......... *A61B 5/14532* (2013.01); *G01D 3/022* (2013.01); *G01D 9/005* (2013.01); *G01K 7/42* (2013.01); *G01N 27/327* (2013.01); *G01N 33/48785* (2013.01); *G01N 33/50* (2013.01); *G01N 33/66* (2013.01); *G16B 20/00* (2019.02)

(56) References Cited

U.S. PATENT DOCUMENTS

| | | | | |
|---|---|---|---|---|
| 6,780,296 B1* | 8/2004 | Bhullar | ............... | G01N 27/3272 204/403.01 |
| 6,880,968 B1* | 4/2005 | Haar | .................. | G01N 21/8483 374/131 |
| 7,875,165 B2 | 1/2011 | Nakasone et al. | | |
| 8,287,704 B2* | 10/2012 | Shinno | ..................... | C12Q 1/54 204/403.02 |
| 8,287,718 B2* | 10/2012 | Shinno | ..................... | C12Q 1/54 204/403.02 |
| 8,783,946 B2 | 7/2014 | Goto | | |
| 9,823,214 B2* | 11/2017 | Ochi | ................. | G01N 27/3274 |
| 9,921,227 B2* | 3/2018 | Matsumura | ........ | G01N 27/3274 |
| 10,094,804 B2* | 10/2018 | Murakoshi | ........ | G01N 27/3274 |
| 10,302,502 B2* | 5/2019 | Kern | ..................... | G05B 15/02 |
| 10,321,844 B2* | 6/2019 | Varsavsky | ............ | A61B 5/1473 |
| 2003/0159945 A1 | 8/2003 | Miyazaki et al. | | |
| 2004/0052291 A1 | 3/2004 | Suurkuusk et al. | | |
| 2004/0076215 A1 | 4/2004 | Baumbach | | |
| 2004/0154932 A1* | 8/2004 | Deng | ................. | G01N 27/3274 205/777.5 |
| 2005/0004717 A1 | 1/2005 | Fukushima et al. | | |
| 2005/0019219 A1* | 1/2005 | Oshiman | .................. | G01K 1/16 422/82.12 |
| 2005/0041722 A1 | 2/2005 | Tokita et al. | | |
| 2005/0054905 A1* | 3/2005 | Corl | .................... | A61B 5/14539 600/309 |
| 2005/0182311 A1* | 8/2005 | Cho | .......................... | A61B 5/01 600/365 |
| 2005/0187442 A1* | 8/2005 | Cho | .......................... | A61B 5/01 600/316 |
| 2005/0250999 A1 | 11/2005 | Cho et al. | | |
| 2006/0079742 A1 | 4/2006 | Cho et al. | | |
| 2006/0080056 A1* | 4/2006 | Takei | ....................... | G01J 5/16 702/99 |
| 2006/0091006 A1* | 5/2006 | Wang | .................... | A61B 5/1486 204/403.02 |
| 2006/0160171 A1* | 7/2006 | Bachur, Jr. | ........... | G01N 27/221 435/34 |
| 2006/0175206 A1 | 8/2006 | Miyazaki et al. | | |
| 2006/0175207 A1 | 8/2006 | Miyazaki et al. | | |
| 2006/0224349 A1 | 10/2006 | Butterfield | | |
| 2006/0229502 A1* | 10/2006 | Pollock | .............. | A61B 5/14532 600/300 |
| 2007/0025877 A1 | 2/2007 | Hansen | | |
| 2007/0038141 A1 | 2/2007 | Koch | | |
| 2007/0135697 A1* | 6/2007 | Reggiardo | ......... | A61B 5/14532 600/347 |
| 2007/0172388 A1* | 7/2007 | Padmanabhan | .... | G01N 15/1459 422/400 |
| 2007/0282180 A1* | 12/2007 | Caduff | ...................... | A61B 5/01 600/316 |
| 2008/0049812 A1 | 2/2008 | Yu | | |
| 2008/0110754 A1 | 5/2008 | Miyazaki et al. | | |
| 2008/0152543 A1 | 6/2008 | Karaki et al. | | |
| 2008/0242962 A1* | 10/2008 | Roesicke | ............ | A61B 5/14532 600/347 |
| 2009/0098657 A1* | 4/2009 | Blais | .................. | G01N 21/8483 436/147 |
| 2009/0236237 A1 | 9/2009 | Shinno et al. | | |
| 2009/0299152 A1* | 12/2009 | Taub | ................... | A61B 5/14532 600/300 |
| 2009/0325205 A1 | 12/2009 | Fujii et al. | | |
| 2010/0036213 A1* | 2/2010 | Rieth | ..................... | A61B 5/4277 600/301 |
| 2010/0100351 A1 | 4/2010 | Kobayashi et al. | | |
| 2010/0128754 A1* | 5/2010 | Jetter | .................. | A61B 5/14532 374/110 |
| 2010/0168537 A1* | 7/2010 | Ueda | ................... | A61B 5/14532 600/365 |
| 2010/0252454 A1 | 10/2010 | Miyazaki et al. | | |
| 2010/0268475 A1 | 10/2010 | Kusumoto | | |
| 2010/0274154 A1 | 10/2010 | Bellifemine | | |
| 2010/0283488 A1* | 11/2010 | Nakamura | ......... | G01N 27/3274 324/692 |
| 2010/0307916 A1* | 12/2010 | Ramey | ................. | A61B 5/6887 204/402 |
| 2010/0320097 A1 | 12/2010 | Miyazaki et al. | | |
| 2010/0328090 A1* | 12/2010 | Hiramatsu | ............ | G01K 13/002 340/687 |
| 2011/0021891 A1 | 1/2011 | Yokoyama et al. | | |
| 2011/0132776 A1 | 6/2011 | Miyazaki et al. | | |
| 2011/0132777 A1 | 6/2011 | Miyazaki et al. | | |
| 2011/0174638 A1* | 7/2011 | Katsuki | ............... | A61B 5/14503 205/792 |
| 2011/0203942 A1 | 8/2011 | Uchiyama | | |
| 2011/0210951 A1* | 9/2011 | Guthrie | ............ | G01N 33/48792 345/204 |
| 2011/0243183 A1 | 10/2011 | Goto | | |
| 2011/0257496 A1* | 10/2011 | Terashima | .......... | A61B 5/14532 600/347 |
| 2011/0272294 A1 | 11/2011 | Fujiwara | | |
| 2011/0297557 A1* | 12/2011 | Wu | ..................... | G01N 27/3274 205/792 |
| 2011/0308321 A1 | 12/2011 | Kasai | | |
| 2012/0043227 A1 | 2/2012 | Miyazaki et al. | | |
| 2012/0103806 A1 | 5/2012 | Shinno et al. | | |
| 2012/0116706 A1* | 5/2012 | Nakanishi | .......... | A61B 5/14532 702/99 |
| 2013/0020208 A1 | 1/2013 | Miyazaki et al. | | |
| 2013/0053661 A1* | 2/2013 | Alberth | ................ | A61B 5/1455 600/322 |
| 2013/0108510 A1* | 5/2013 | Takeuchi | ............ | G01N 27/3273 422/82.12 |
| 2013/0197847 A1* | 8/2013 | Tsukada | ............. | A61B 5/1495 702/104 |
| 2013/0261414 A1* | 10/2013 | Tai | ..................... | A61B 5/02427 600/324 |
| 2013/0279539 A1* | 10/2013 | Matsumura | ........ | G01N 27/3274 374/208 |
| 2013/0334041 A1* | 12/2013 | Kondo | ............... | G01N 33/4875 204/403.01 |
| 2014/0012116 A1* | 1/2014 | Okuyama | .......... | A61B 5/14532 600/347 |
| 2014/0036956 A1 | 2/2014 | Goto | | |
| 2014/0118104 A1* | 5/2014 | Sicurello | ............ | A61B 5/0015 340/3.1 |
| 2014/0177671 A1* | 6/2014 | Watanabe | ............ | G01N 27/28 374/142 |
| 2014/0355649 A1* | 12/2014 | Niederberger | ....... | G01D 3/0365 374/152 |

(56) References Cited

U.S. PATENT DOCUMENTS

| | | | | |
|---|---|---|---|---|
| 2015/0309010 | A1* | 10/2015 | Furukawa | A61B 5/145 |
| | | | | 702/19 |
| 2017/0131232 | A1* | 5/2017 | Murakoshi | G01N 27/3274 |
| 2017/0254773 | A1* | 9/2017 | Uchiyama | G01N 27/3274 |

FOREIGN PATENT DOCUMENTS

| | | |
|---|---|---|
| JP | H11-239201 A | 8/1999 |
| JP | 2003-156469 A | 5/2003 |
| JP | 2004-023317 A | 1/2004 |
| JP | 2004-325110 A | 11/2004 |
| JP | 2011-095279 A | 5/2011 |
| JP | 2011-137769 A | 7/2011 |
| JP | 2011-215107 A | 10/2011 |
| JP | 4930642 B2 | 5/2012 |
| WO | 2005/000114 A2 | 1/2005 |
| WO | 2005/001680 A1 | 1/2005 |
| WO | 2008/004565 A1 | 1/2008 |
| WO | 2009/119116 A1 | 10/2009 |

OTHER PUBLICATIONS

Decision to grant a Patent from the corresponding Japanese Patent Application No. 2013-541603 dated Apr. 28, 2015.
Office Action from the corresponding Japanese Patent Application No. 2015-098997 dated Mar. 22, 2016.
The Office Action from the co-pending U.S. Appl. No. 14/354,132 dated Feb. 9, 2017.
The Notice of Allowance from the co-pending U.S. Appl. No. 14/354,132 dated Aug. 11, 2017.

* cited by examiner

BIOLOGICAL SAMPLE MEASURING APPARATUS

PRIORITY

This application is a continuation application of and claims priority to U.S. application Ser. No. 14/354,132 filed on Apr. 24, 2014, which is a National Stage Application under 35 U.S.C. § 365 to International Application PCT/JP2012/006762, with an international filing date of Oct. 23, 2012, which claims priority to Japanese Patent Application No. 2011-239996 filed on Nov. 1, 2011 and Japanese Patent Application No. 2011-239997 filed on Nov. 1, 2011. The entire disclosures of U.S. application Ser. No. 14/354,132, International Application PCT/JP2012/006762, Japanese Patent Application No. 2011-239996, and Japanese Patent Application No. 2011-239997 are hereby incorporated herein by reference.

TECHNICAL FIELD

The present invention relates to a biological sample measuring apparatus that measures biological sample information such as a blood glucose level or a lactic acid level from a biological sample.

BACKGROUND

Conventional biological sample measuring apparatuses have been configured so as to have a body case having a biological sample sensor mounting portion on one end side, a temperature sensor provided on the one end side inside the body case, a measurement portion connected to the biological sample sensor mounting portion, and a control portion connected to the measurement portion.

Specifically, a blood glucose level sensor, which is one example of a biological sample sensor, is mounted to the biological sample mounting portion, and the measurement value obtained by the measurement portion is corrected based on a detection temperature (temperature information) detected by the temperature sensor so as to obtain a measured blood glucose level (e.g., see Patent Literature 1: WO 2005/000114).

One issue in the above conventional example is that measurement error occurs.

Specifically, conventional biological sample measuring apparatuses are widely utilized in hospitals, for example, and measurement is carried out on multiple patients consecutively.

In such a situation, one biological sample measuring apparatus is used by multiple users (nurses or the like), and whereas some people may grip one end side of the body case during use, other people may grip the other end side of the body case during use.

Here, if measurement is carried out multiple times consecutively while gripping one end side of the body case, for example, there are cases where heat from the gripping hand will gradually be transmitted to the interior of the body case and influence the detection temperature (temperature information) detected by the temperature sensor provided inside the body case.

Thus, there has been the danger of a large measurement error occurring if the temperature correction of the measurement value described above is performed using a temperature influenced in this way.

SUMMARY

The present invention includes a body case having a biological sample sensor mounting portion on one end side, a first temperature sensor provided on the one end side inside the body case, a measurement portion connected to the biological sample sensor mounting portion, and a control portion connected to the measurement portion. A second temperature sensor is provided on one other end side inside the body case, and when biological sample information measurement is performed in the measurement portion, temperature change amounts in two end portions of the body case are compared using the first and second temperature sensors. A biological sample information measurement value in the measurement portion is corrected using temperature information from either one of the first or second temperature sensors that is provided in either one of the two end portions where temperature change is smaller.

According to the present invention, a biological sample information measurement value in the measurement portion is corrected using temperature information from either one of the first and second temperature sensors that is provided in the end portion where temperature change is smaller, and therefore it is possible to suppress measurement error.

As a result, with the present invention, the measurement value can be corrected using temperature information that was much less influenced by heat from the user's hand, thus making it possible to suppress measurement error.

DETAILED DESCRIPTION

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

First Embodiment

A biological sample measuring apparatus according to a first embodiment of the present invention will be described below with reference to the drawings, taking the example of a biological sample measuring apparatus for measuring a blood glucose level in a hospital, for example.

Figure 1:
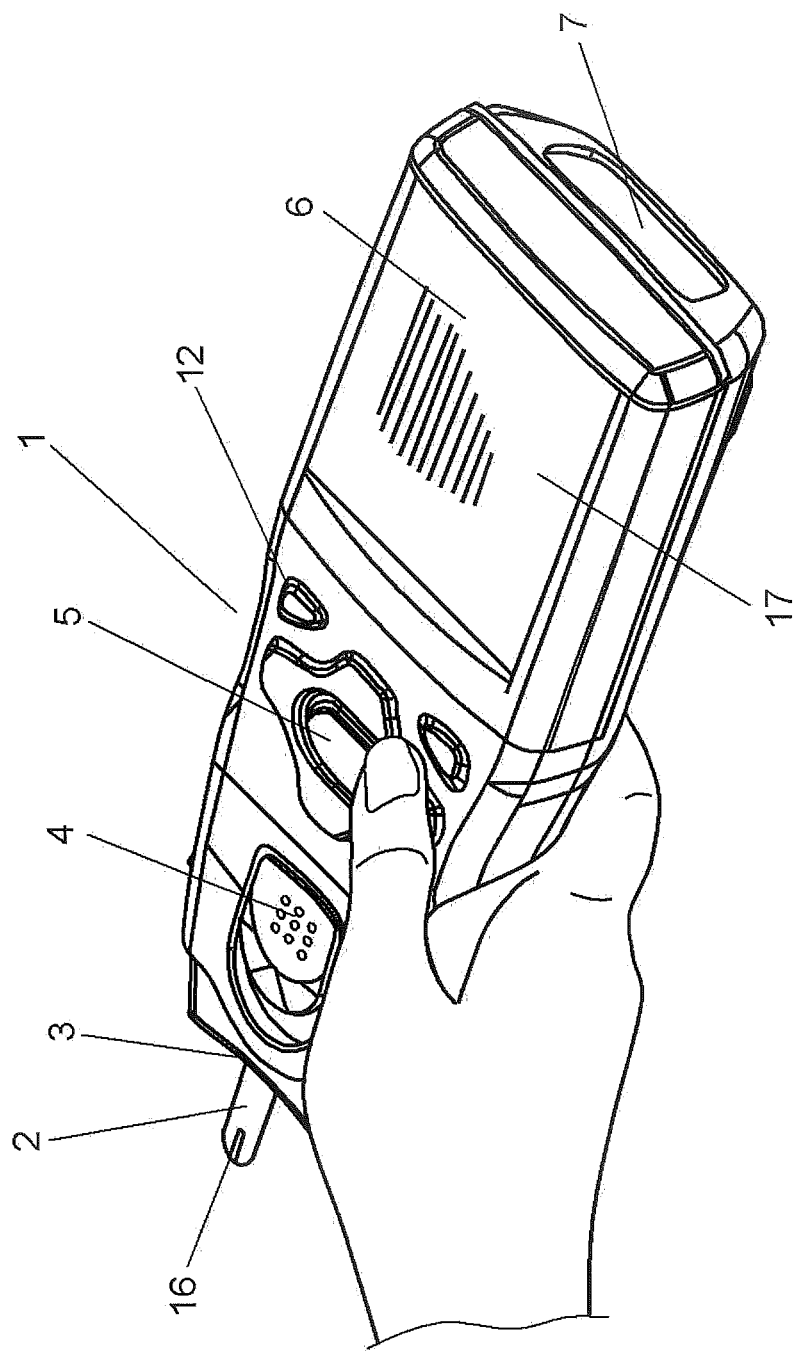
FIG. 1 is a perspective view of a biological sample measuring apparatus.
Figure 3:
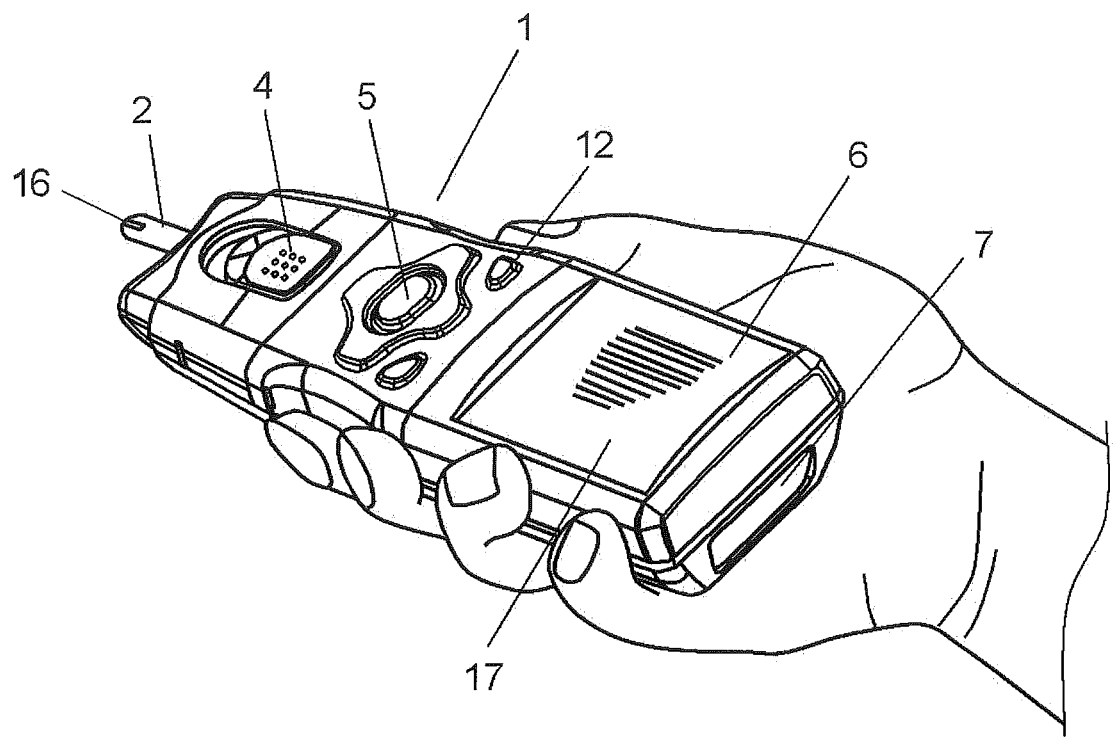
FIG. 3 is a perspective view of a biological sample measuring apparatus.

As shown in FIGS. 1 and 3, a biological sample sensor mounting portion 3 for mounting a blood glucose level sensor 2, which is one example of a biological information measurement sensor, is provided on one end side of a substantially rectangular body case 1. Also, a sensor discharge lever 4 is arranged on the surface of the one end side of the body case 1, an operation portion 5 is arranged in the central portion, and a display portion 6 is arranged on the other end side. Furthermore, a laser-type barcode reader 7 for scanning various types of IDs (e.g., a user ID, a patient ID, and the ID of the blood glucose level sensor 2) is provided on the other end side of the body case 1.

Figure 2:
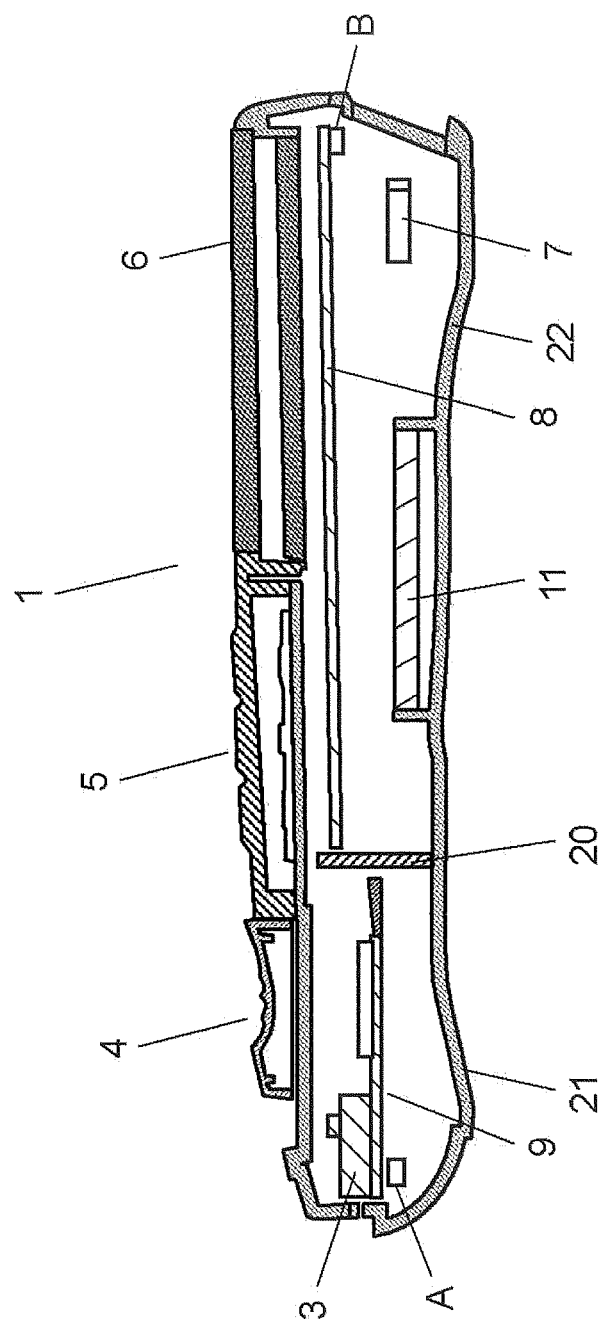
FIG. 2 is a cross-sectional view of a biological sample measuring apparatus.

FIG. 2 is a cross-sectional view of the body case 1. A control board 8 is stored inside the body case 1, in a portion corresponding to the display portion 6 and the operation portion 5. Furthermore, a measurement board 9 is stored inside the body case 1, in a portion corresponding to the sensor discharge lever 4 and the biological sample sensor mounting portion 3.

Figure 4:
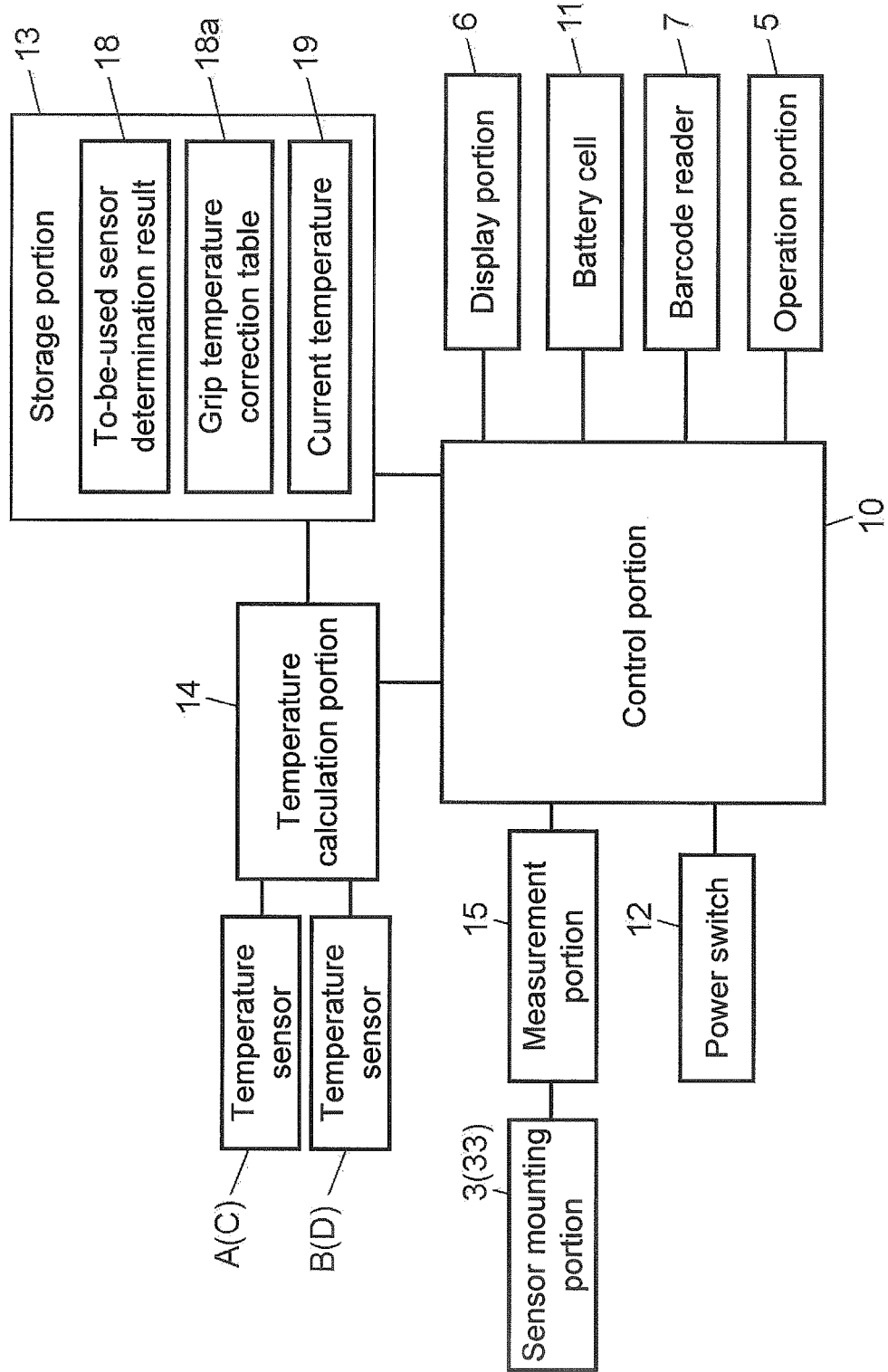
FIG. 4 is a control block diagram of a biological sample measuring apparatus.

The control board 8 mainly comprises a control portion 10 shown in FIG. 4, and the operation portion 5, the display portion 6, the barcode reader 7, a battery cell 11, and a power switch 12 are connected to the control portion 10. Furthermore, a temperature calculation portion 14 is connected to the control portion 10 via a storage portion 13, and a temperature sensor A and a temperature sensor B are connected to the temperature calculation portion 14. Note that the temperature calculation portion 14 is also directly connected to the control portion 10.

Meanwhile, the measurement board 9 in FIG. 2 mainly comprises the measurement portion 15, and as shown in FIG. 4, the biological sample sensor mounting portion 3 is electrically connected to the measurement portion 15. Also, the measurement portion 15 and the control portion 10 are electrically connected.

Figure 5:
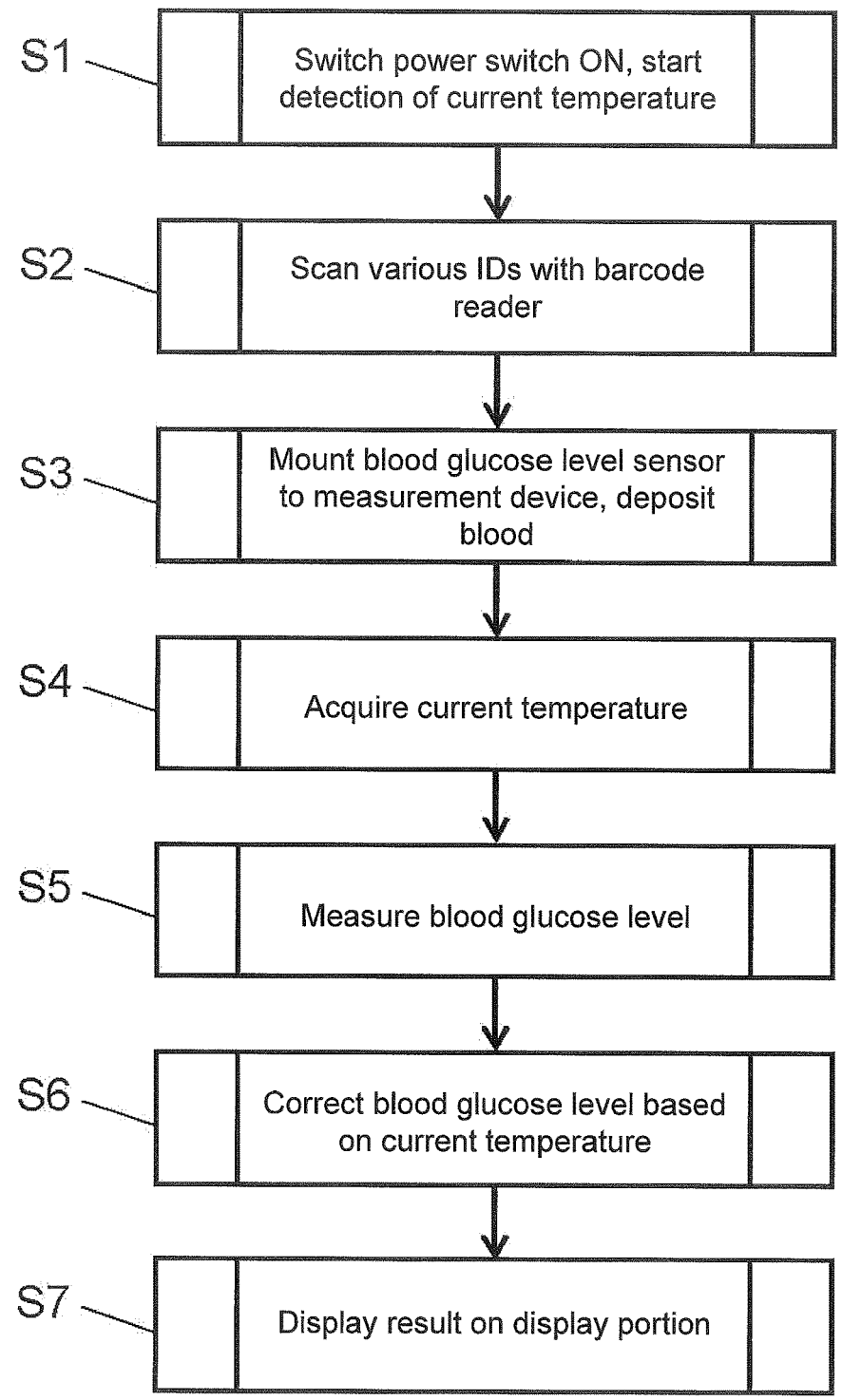
FIG. 5 is a control flowchart of a biological sample measuring apparatus.

When the user switches on the power switch 12, the temperature calculation portion 14 starts detecting the current temperature inside the body case 1 using the temperature sensor A and the temperature sensor B in order to estimate the environmental temperature outside the body case 1 (step S1 in FIG. 5). The detection of the current temperature will be described in detail later.

Next, the user scans various types of IDs such as a user ID, a patient ID, and the ID of the blood glucose level sensor 2 using the barcode reader 7 (step S2 in FIG. 5). Thereafter, the user connects a connection terminal (not shown) provided on the other end side of the blood glucose level sensor 2 to the biological sample sensor mounting portion 3 as shown in FIG. 1. In this state, blood is deposited on a deposit portion 16 in FIG. 1 that is provided on the one end side of the blood glucose level sensor 2 (step S3 in FIG. 5).

Thereafter, the control portion 10 in FIG. 4 acquires the aforementioned current temperature that was detected by the temperature calculation portion 14 (step S4 in FIG. 5). Next, the measurement portion 15 measures the blood glucose level (step S5 in FIG. 5), and the control portion 10 corrects the blood glucose level based on the current temperature (step S6 in FIG. 5).

As is well-known, the reaction in the blood glucose level sensor 2 varies greatly depending on the temperature at this time, and therefore the blood glucose level is corrected based on the current temperature. For this reason, it is important to detect an accurate current temperature.

The corrected result is then displayed on the display portion 6 (step S7 in FIG. 5).

Note that a protective film 17 for scratch prevention is provided on the surface of the display portion 6 as shown in FIG. 1.

A characteristic point of the present embodiment is that the temperature sensor A is provided on the one end side inside the substantially rectangular body case 1, and the temperature sensor B is provided on the other end side as shown in FIG. 2.

Specifically, the biological sample measuring apparatus of the present embodiment will be widely utilized in hospitals, for example, and a single biological sample measuring apparatus will be used by multiple users (nurses or the like) in such places as hospitals. In this usage situation, some people will grip the one end side of the body case 1 during use as shown in FIG. 1, and other people will grip the other end side of the body case 1 during use as shown in FIG. 3. Measurement will be carried out on multiple patients consecutively in this state. Accordingly, heat from the user's hand will be transmitted to the interior of the end portion on the gripped side of the body case 1, and the detection temperature (temperature information) at that end portion will change greatly.

In view of this, the measurement value obtained by the measurement portion 15 is corrected using the temperature information from either one of the temperature sensor A or the temperature sensor B that is provided in the end portion on the side opposite to the end portion corresponding to temperature information having a larger temperature change amount, that is to say, the one that is provided in the end portion where the temperature change is smaller.

As a result, the measurement value can be corrected using temperature information that was much less influenced by heat from the user's hand, thus making it possible to suppress measurement error.

Note that as shown in FIG. 2, the temperature sensor A and the temperature sensor B are provided in the vicinity of the outer wall at the respective end portions of the body case 1. For this reason, the temperature sensor A and the temperature sensor B similarly follow changes in the outside environmental temperature such that temperature differences do not occur in the detection temperatures obtained by the two temperature sensors.

Figure 6:
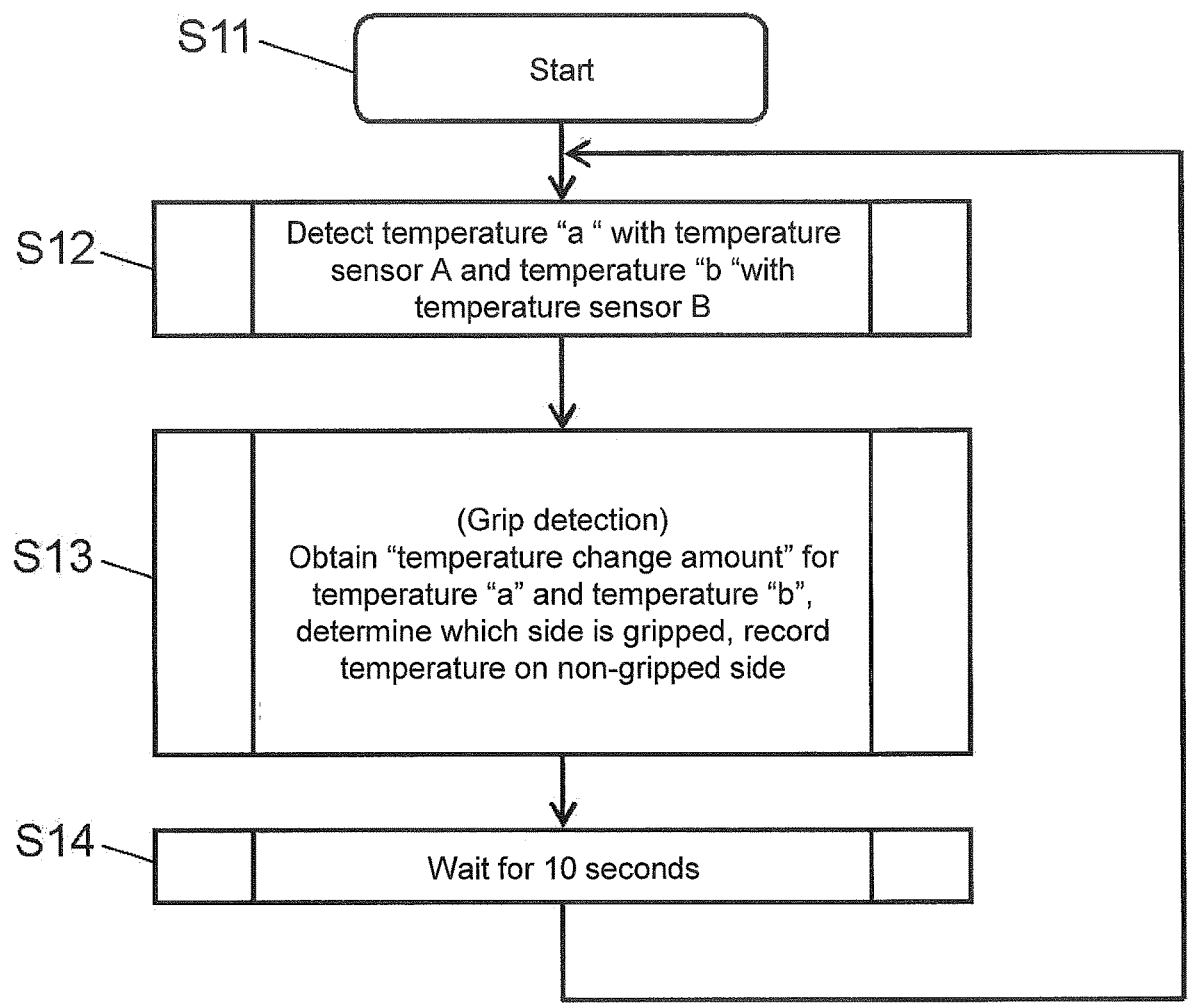
FIG. 6 is a control flowchart of a biological sample measuring apparatus.

The following describes operations of the temperature sensor A and the temperature sensor B taking the example of the case where the user grips the one end side of the body case 1, that is to say the temperature sensor A side, during use as shown in FIG. 1, with reference to FIGS. 4 and 6.

First, when the user switches on the power switch 12, the control portion 10 starts to detect the temperature inside the body case 1 using the temperature calculation portion 14 (step S11 in FIG. 6). The temperature calculation portion 14 detects a temperature "a" inside the one end side of the body case 1 and a temperature "b" inside the other end side of the body case 1 using the temperature sensor A and the temperature sensor B (step S12 in FIG. 6).

Here, depending on the relationship between the user's body temperature and the usage environmental temperature, there are cases where the user's hand is a heat generator and cases where the user's hand is a heat absorber that lowers the internal temperature of the body case 1. Which it acts as is determined by the ambient temperature (outside air temperature) around the body case 1. This point will be described below with reference to FIG. 7.

Figure 7:
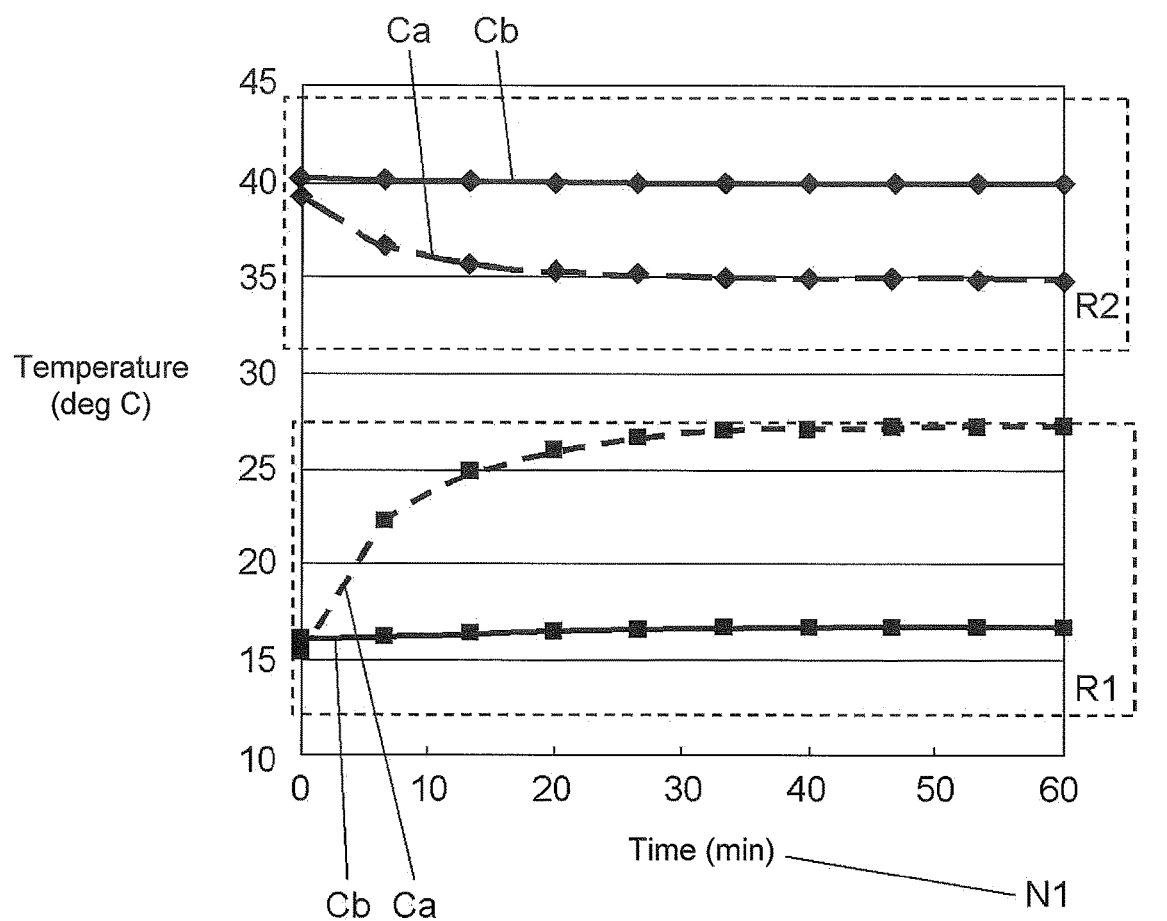
FIG. 7 is a diagram showing internal temperature change during use of a biological sample measuring apparatus.

FIG. 7 shows the relationship that a detection temperature Ca from the temperature sensor A and a detection temperature Cb from the temperature sensor B have with a grip time N1, which is the length of time that the user grips the body case 1.

First, the case where the user's hand acts as a pseudo heat generator will be described.

A region R1 at the bottom of FIG. 7 shows the relationship between the detection temperature Ca (temperature sensor A) and the detection temperature Cb (temperature sensor B) when the ambient temperature is low (e.g., 16° C.). Specifically, this region shows the relationship when the ambient temperature was 16° C., the user gripped the one end side with a hand temperature of 34° C., and measurement was carried out multiple times consecutively.

At this low temperature, the temperature of the user's hand is higher than the ambient temperature, and therefore heat from the user's hand raises the internal temperature of the body case 1. In other words, the user's hand is a pseudo heat generator.

Accordingly, as shown in the region R1 in FIG. 7, the longer the grip time N1 is, the more heat from the hand is transmitted into the one end side of the body case 1, and the more the detection temperature Ca from the temperature sensor A changes so as to rise. On the other hand, the detection temperature Cb from the temperature sensor B provided on the other end side is in a substantially constant state due to not being influenced by heat from the hand.

Next, the case where the user's hand acts as a pseudo heat absorber will be described.

A region R2 at the top of FIG. 7 shows the relationship between the detection temperature Ca (temperature sensor A) and the detection temperature Cb (temperature sensor B) when the ambient temperature is high (e.g., 40° C.). Specifically, this region shows the relationship when the ambient temperature was 40° C., the user gripped the one end side with a hand temperature of 32° C., and measurement was carried out multiple times consecutively.

At this high temperature, the temperature of the user's hand is lower than the ambient temperature, and therefore the user's hand steals heat from the body case 1 so as to lower the internal temperature. In other words, the user's hand is a pseudo heat absorber.

Accordingly, as shown in the region R2 in FIG. 7, the longer the grip time N1 is, the more heat inside the body case 1 is absorbed by the user's hand, and the more the detection temperature Ca from the temperature sensor A on the one end side changes so as to decrease, whereas the detection temperature Cb from the temperature sensor B on the other end side is in a substantially constant state due to not being influenced by heat from the hand.

In this way, both when the user's hand is a pseudo heat generator and when it is a pseudo heat absorber, the temperature obtained by the temperature sensor provided on the one end side gripped by the user (the temperature sensor A in this case) changes greatly.

In view of this, the temperature calculation portion 14 does not use the temperature information from the temperature sensor A on the one end side where the temperature change is large (temperature "a"), and records the temperature sensor B provided in the end portion on the opposite side as the sensor to be used in a to-be-used sensor determination result area 18 in the storage portion 13.

The temperature information from the temperature sensor B (temperature "b") is then recorded as the current temperature in a current temperature area 19 (step S13 in FIG. 6).

The control portion 10 then acquires the current temperature from the current temperature area 19 and corrects the blood glucose level obtained by the measurement portion 15 using the current temperature (step S6 in FIG. 5) as described above.

In this way, the measurement value can be corrected using the temperature information from the temperature sensor B on the side that was much less influenced by heat from the user's hand, thus making it possible to suppress measurement error.

Then, after waiting for 10 seconds (10-second wait) (step S14 in FIG. 6), the procedure returns to step S12 in FIG. 6, and the measurement of the current temperature is started again. The processing of steps S12 to S14 in FIG. 6 is repeated until the user switches off the power switch 12, and therefore the control portion 10 can always acquire the most recent current temperature from the current temperature area 19 of the storage portion 13.

Note that the above description was given taking the example where the user grips the one end side, that is to say the temperature sensor A side, of the body case 1 during use as shown in FIG. 1. However, there are also cases where the user grips the other end side, that is to say the temperature sensor B side, of the body case 1 during use as shown in FIG. 3.

In this case, heat from the user's hand will be transmitted to the interior of the end portion on the temperature sensor B side, and the detection temperature Cb at that end portion will change greatly.

For this reason, the measurement value obtained by the measurement portion 15 is corrected using the temperature information from the temperature sensor A provided in the end portion on the side opposite to the temperature sensor B side where the temperature change is large.

Furthermore, in the present embodiment, a partition 20 is provided between an accommodating portion for the temperature sensor A on the one end side of the body case 1 and an accommodating portion for the temperature sensor B on the other end side as shown in FIG. 2. Accordingly, heat exchange (movement of heat) between the one end side and the other end side can be disrupted, and it is possible to effectively suppress the influence that heat from the user's hand that was transmitted to one side has on the other side.

As a result, the measurement value can be corrected using temperature information from either one of the temperature sensor A or the temperature sensor B that is on the side that was much less influenced by heat from the user's hand, thus making it possible to suppress measurement error.

Furthermore, in the present embodiment, a protruding portion 21 and a protruding portion 22 are formed such that portions on the underside of the body case 1 that correspond to the temperature sensor A and the temperature sensor B protrude downward.

The user will naturally grip the protruding portion 21 and the protruding portion 22.

For this reason, the user will grip the periphery of the temperature sensor A or the temperature sensor B in a natural manner, and the temperature sensor A or the temperature sensor B can effectively sense heat from the user's hand.

Note that although the present embodiment is configured such that temperature measurement is performed by the temperature sensors A and B before the measurement of biological sample information, and the immediately previous temperature information is utilized, a configuration is possible in which the temperature measurement is performed by the temperature sensors A and B when biological sample information is measured.

Second Embodiment

Figure 9:
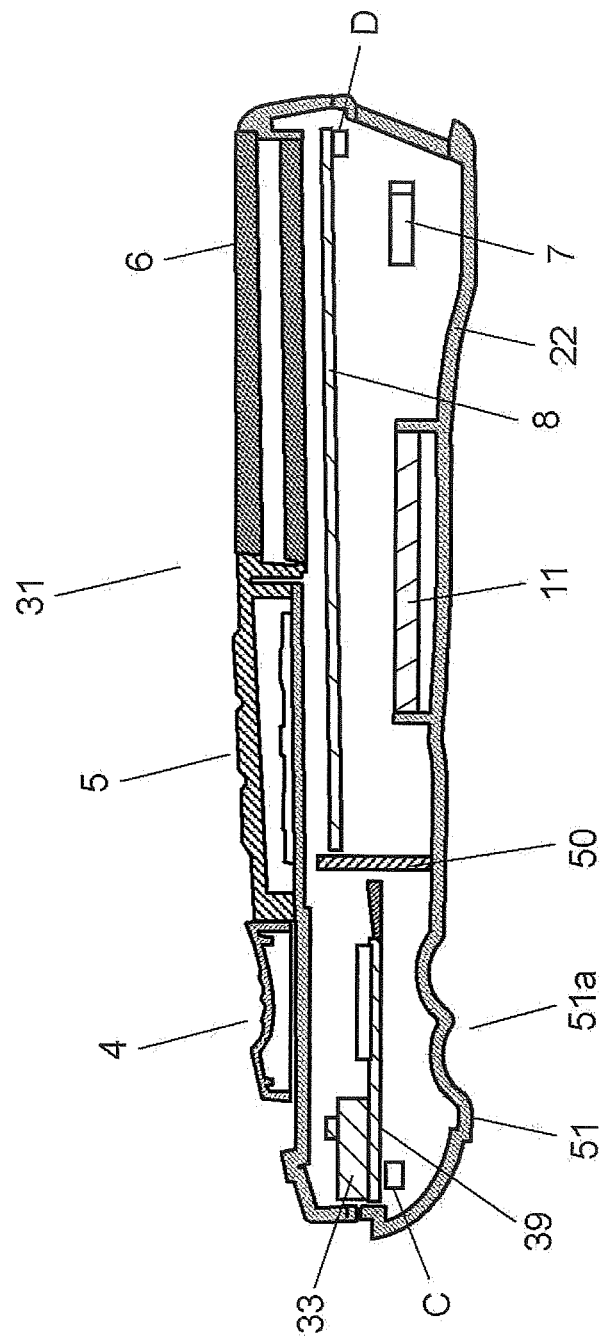
FIG. 9 is a cross-sectional view of a biological sample measuring apparatus.

Differences between a biological sample measuring apparatus according to a second embodiment of the present invention and the biological sample measuring apparatus of the first embodiment will be described below. As shown in FIG. 9, the biological sample measuring apparatus of the present embodiment has a grip portion 51a obtained by forming recessed finger grooves that conform to the bulging of fingers on a protruding portion 51 on the underside portion of a body case 31. This clearly indicates the portion that is to be gripped, and the user will naturally grip the grip portion 51a. In this way, with the biological sample measuring apparatus according to the second embodiment of the present invention, the portion gripped by the user is fixed on the one end side.

Furthermore, a temperature detection sensor D that detects the usage environmental temperature (current temperature) is provided inside the body case 31 on the side (the other end side) opposite to the grip portion 51a on the one end side. Also, a temperature correction sensor C for correcting the influence of heat from the user's hand is provided inside the body case 31 in correspondence with the grip portion 51a on the one end side.

Note that as shown in FIG. 9, the temperature correction sensor C and the temperature detection sensor D are provided in the vicinity of the outer wall at the respective end portions of the body case 31. For this reason, the temperature correction sensor C and the temperature detection sensor D similarly follow changes in the outside environmental temperature such that temperature differences do not occur in the detection temperatures obtained by the two temperature sensors.

Specifically, the biological sample measuring apparatus of the present embodiment will be widely utilized in hospitals, for example, and the grip portion 51a on the one end side of the body case 31 will be gripped during use.

In order to make heat from the hand holding the grip portion 51a unlikely to be transmitted to the temperature detection sensor D, the temperature detection sensor D is arranged on the other end side of the body case 31 as shown in FIG. 9.

However, even with this countermeasure, if nurses carry out measurement on multiple patients consecutively in a hospital, for example, heat from the hand gripping the grip portion 51a will accumulate inside the grip portion 51a. As a result of meeting demand for a reduction in the size of biological sample measuring apparatuses in recent years, there are some cases where the detection temperature (temperature information) from the temperature detection sensor D provided in the end portion on the side opposite to the grip portion 51a is also influenced, although to a slight degree.

In view of this, in the present embodiment, the detection temperature from the temperature detection sensor D on the other end side is corrected using temperature information from the temperature correction sensor C on the one end side.

Accordingly, the measurement value obtained by the measurement portion 15 shown in FIG. 4 is corrected using temperature information obtained by correcting the detection temperature from the temperature detection sensor D provided in the end portion on the other end side where the temperature change is small, and therefore a measurement result with very little influence from heat from the user's hand is obtained.

As a result, it is possible to suppress measurement error.

Figure 8:
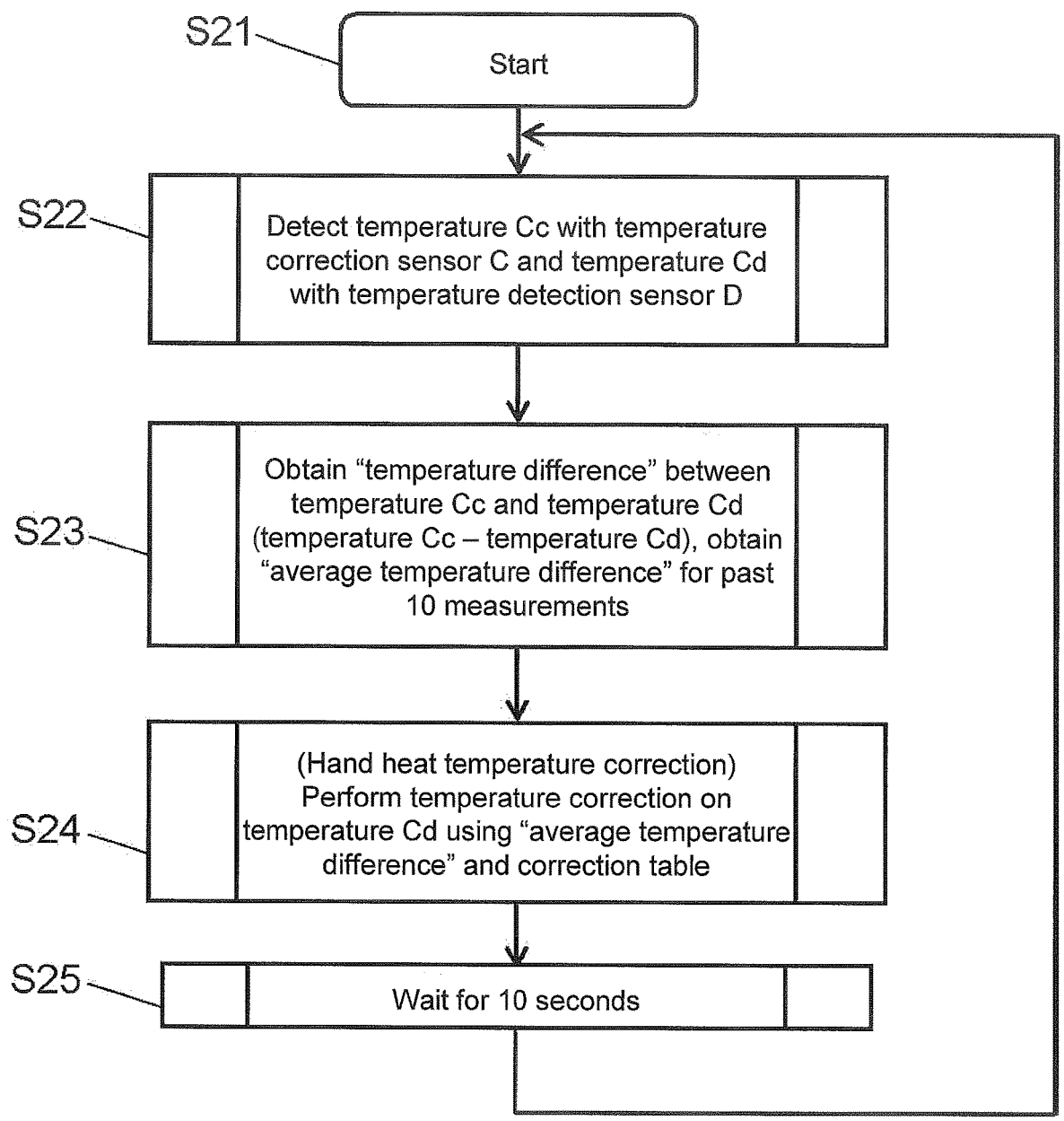
FIG. 8 is a control flowchart of a biological sample measuring apparatus.

The following describes the correction of the temperature detection sensor D using the temperature information from the temperature correction sensor C with reference to FIGS. 4 and 8.

First, when the user switches on the power switch 12, the control portion 10 starts to detect the temperature inside the body case 1 using the temperature calculation portion 14 (step S21 in FIG. 8).

The temperature calculation portion 14 detects a temperature Cc inside the one end side and a temperature Cd inside the other end side using the temperature correction sensor C and the temperature detection sensor D (step S22 in FIG. 8).

Here, depending on the relationship between the user's body temperature and the usage environmental temperature, there are cases where the user's hand is a pseudo heat generator and cases where the user's hand is a pseudo heat absorber that lowers the temperature inside the body case 31.

Which it acts as is determined by the ambient temperature (outside air temperature) around the body case 31. This will be described below with reference to FIG. 10.

Figure 10:
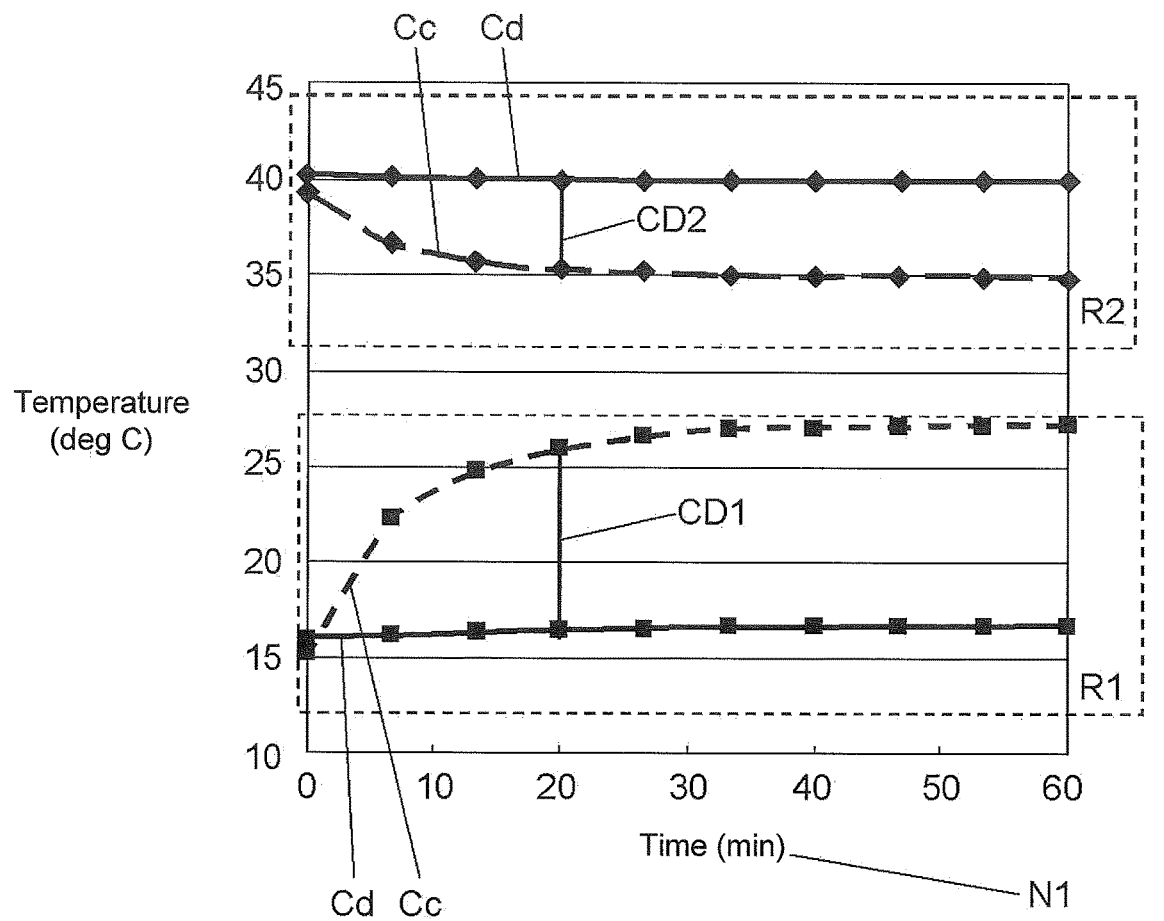
FIG. 10 is a diagram showing internal temperature change during use of a biological sample measuring apparatus.

FIG. 10 shows the relationship that the detection temperature Cc from the temperature correction sensor C and the detection temperature Cd from the temperature detection sensor D have with the grip time N1, which is the length of time that the user grips the grip portion 51a of the body case 31.

First, the case where the user's hand is a pseudo heat generator will be described.

A region R1 at the bottom of FIG. 10 shows the relationship between the detection temperature Cc (temperature correction sensor C) and the detection temperature Cd (temperature detection sensor D) when the ambient temperature is low (e.g., 16° C.). Specifically, this region shows the relationship when the ambient temperature was 16° C., the user gripped the grip portion 51a on the one end side with a hand temperature of 34° C., and measurement was carried out multiple times consecutively.

At this low temperature, the temperature of the user's hand is higher than the ambient temperature, and therefore heat from the user's hand raises the internal temperature of the body case 31. In other words, the user's hand is a pseudo heat generator.

For this reason, as shown in the region R1 in FIG. 10, the longer the grip time N1 is due to multiple consecutive measurements, the more heat from the hand is transmitted into the grip portion 51a on the one end side of the body case 31, and the more the detection temperature Cc from the temperature correction sensor C changes so as to rise.

On the other hand, the detection temperature Cd (temperature detection sensor D) shown in the region R1 in FIG. 10 is thought to be constant at around 16 degrees (outside air temperature), for example.

Figure 11:
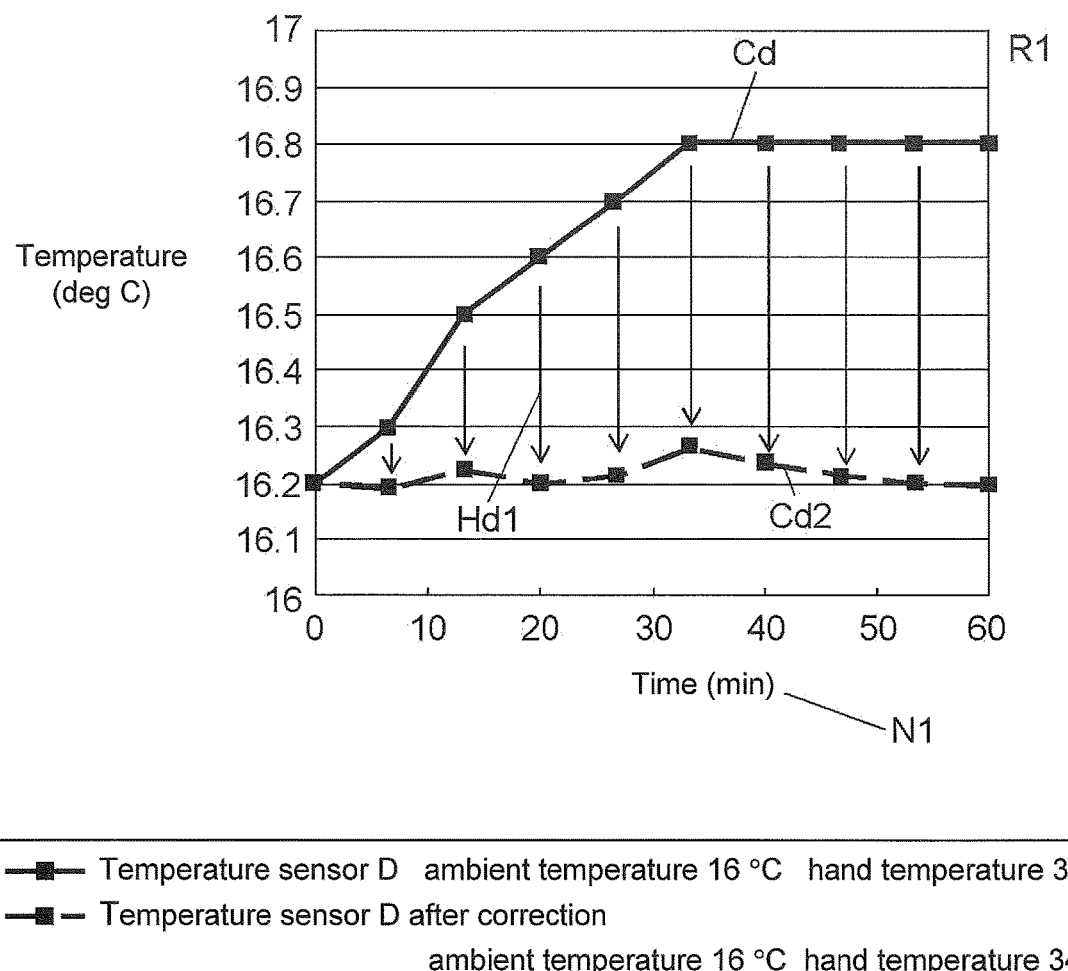
FIG. 11 is a diagram showing internal temperature change during use of a biological sample measuring apparatus.

However, in actuality, heat from the hand gripping the grip portion 51a is gradually transmitted to the temperature detection sensor D portion. This is because the heat from the hand is transmitted along the outer wall constituting the outer surface of the body case 31, a substrate 39 on which the temperature correction sensor C is arranged inside the body case 31, and the like. As a result, the detection temperature Cd (temperature detection sensor D) gradually rises from 16.2 degrees to 16.8 degrees as shown in FIG. 11. Note that FIG. 11 is an enlarged view of the detection temperature Cd in the region R1 corresponding to the low temperature in FIG. 10.

Next, the case where the user's hand is a pseudo heat absorber will be described.

A region R2 at the top of FIG. 10 shows the relationship between the detection temperature Cc (temperature correction sensor C) and the detection temperature Cd (temperature detection sensor D) when the ambient temperature is high (e.g., 40° C.).

Specifically, this region shows the relationship between the detection temperature Cc and the detection temperature Cd when the ambient temperature was 40° C., the user gripped the grip portion 51a on the one end side with a hand temperature of 32° C., and measurement was carried out multiple times consecutively.

At this high temperature, the temperature of the user's hand is lower than the ambient temperature, and therefore the user's hand steals heat from the body case 31 so as to lower the internal temperature. In other words, the user's hand is a pseudo heat absorber.

For this reason, as shown in a region R2 in FIG. 10, the longer the grip time N1 is, the more heat inside the body case 31 is absorbed by the user's hand, and the more the detection temperature Cc from the temperature correction sensor C on the one end side changes so as to decrease.

At this high temperature, the detection temperature Cd (temperature detection sensor D) is thought to be constant at around 40 degrees (outside air temperature), for example, as shown in the region R2 in FIG. 10.

Figure 12:
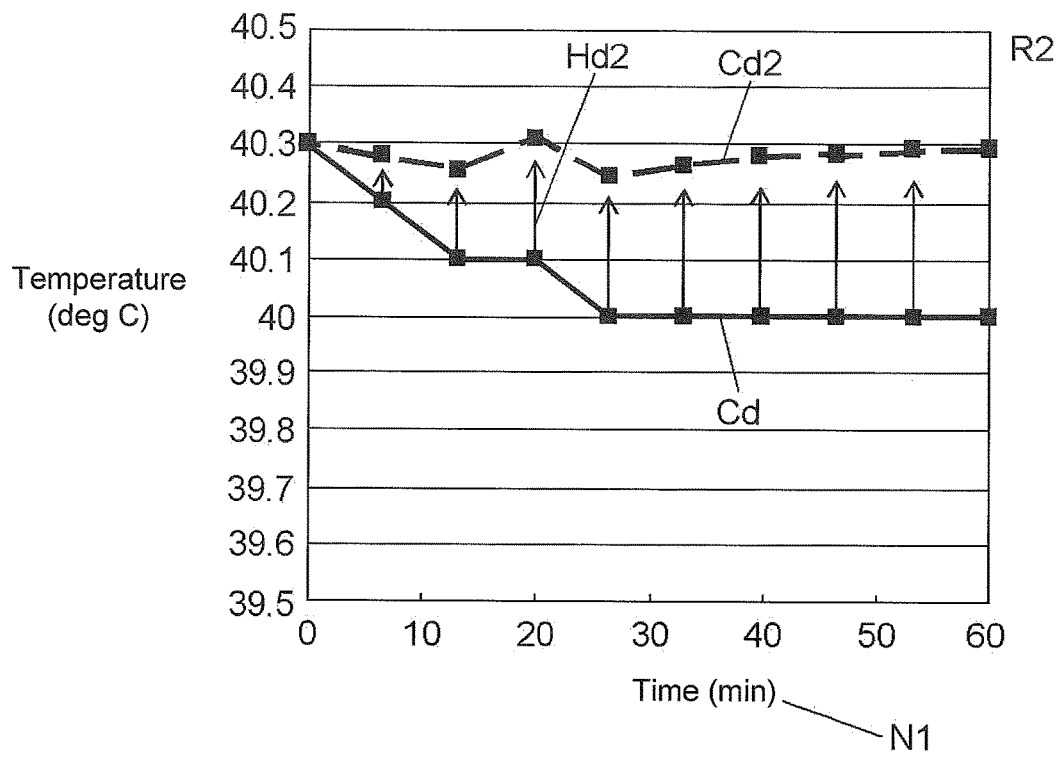
FIG. 12 is a diagram showing internal temperature change during use of a biological sample measuring apparatus.

However, in actuality, heat from the hand gripping the grip portion 51a gradually absorbs heat inside the body case 31, and the detection temperature Cd (temperature detection sensor D) gradually decreases from 40.3 degrees to 40 degrees as shown in FIG. 12. Note that FIG. 12 is an enlarged view of the detection temperature Cd in the region R2 corresponding to the high temperature in FIG. 10.

As described above, heat from the user's hand gripping the grip portion 51a on the one end side reaches the temperature detection sensor D and, although to a slight degree, influences the detection temperature Cd as shown in FIGS. 10 and 11.

In the present embodiment, the detection temperature from the temperature detection sensor D on the other end side is corrected using the temperature information from the temperature correction sensor C on the one end side, and the measurement value obtained by the measurement portion 15 shown in FIG. 4 is corrected based on the corrected detection temperature.

Firstly, the temperature difference between the detection temperature Cc (temperature correction sensor C) and the detection temperature Cd (temperature detection sensor D) is in a certain relationship with the temperature change amount in the detection temperature Cd (temperature detection sensor D).

For example, with the grip time of 20 minutes at the low temperature, a temperature difference CD1 between the detection temperature Cc and the detection temperature Cd in the region R1 in FIG. 10 is in a certain relationship with a temperature change amount Hd1 of the detection temperature Cd (FIG. 11).

Similarly, with the grip time of 20 minutes at the high temperature, for example, a temperature difference CD2 between the detection temperature Cc and the detection temperature Cd in the region R2 in FIG. 10 is in a certain relationship with a temperature change amount Hd2 of the detection temperature Cd as well (FIG. 12).

These relationships are determined by the configuration of the biological sample measuring apparatus. The distance from the grip portion 51a on the one end side gripped by the user to the temperature correction sensor C, the distance from the grip portion 51a on the one end side to the temperature detection sensor D, the arrangement of parts in the body case 31 and the like are elements of the configuration of the biological sample measuring apparatus.

In view of this, in the present embodiment, before the user carries out measurement, the temperature difference CD1 or CD2 in the detection temperatures from the temperature correction sensor C and the temperature detection sensor D when the grip portion 51a on the one end side is gripped, and the temperature change amount Hd1 or Hd2 of the temperature detection sensor D that corresponds to the temperature difference are actually measured for each grip time N1. These actually measured values are then stored in a grip temperature correction table 18a in the storage portion 13 shown in FIG. 4.

Then, in step S23 in FIG. 8 during measurement, the temperature calculation portion 14 obtains the past 10 temperature differences between the detection temperature Cc from the temperature correction sensor C and the detection temperature Cd from the temperature detection sensor D (detection temperature Cc–detection temperature Cd), and obtains an average temperature difference for the detection temperature Cc and the detection temperature Cd by averaging these 10 temperature differences.

Regarding the temperature differences (detection temperature Cc–detection temperature Cd) obtained here in the present embodiment, as shown in the region R1 in FIG. 10, for example, when the hand is a pseudo heat generator at the low temperature, the detection temperature Cc detected by the temperature correction sensor C is higher than the detection temperature Cd detected by the temperature detection sensor D, and the average temperature difference (detection temperature Cc–detection temperature Cd) is a positive value.

Accordingly, the temperature calculation portion 14 performs correction by obtaining the temperature change amount of the temperature detection sensor D that corresponds to the average temperature difference from the grip temperature correction table 18a, and subtracting it from the temperature Cd from the temperature detection sensor D as shown in FIG. 11.

Accordingly, temperature correction is performed as shown by the detection temperature Cd2 in FIG. 11, and the influence of heat from the user's hand due to prolonged repeated use can be excluded.

On the other hand, as shown in the region R2 in FIG. 10, for example, when the hand is a pseudo heat absorber at the high temperature, the detection temperature Cc detected by the temperature correction sensor C is lower than the detection temperature Cd detected by the temperature detection sensor D, and the average temperature difference (detection temperature Cc–detection temperature Cd) is a negative value.

Accordingly, the temperature calculation portion 14 performs correction by obtaining the temperature change amount of the temperature detection sensor D that corresponds to the average temperature difference from the grip temperature correction table 18a, and adding it to the temperature Cd from the temperature detection sensor D as shown in FIG. 12.

Accordingly, temperature correction is performed as shown by the detection temperature Cd2 shown in FIG. 12, and in this case as well, the influence of heat from the user's hand due to prolonged repeated use can be excluded.

In other words, in both the case where the hand gripping the grip portion 51a is a pseudo heat generator and the case where it is a pseudo heat absorber, the temperature Cd can be appropriately subjected to temperature correction, and the influence of heat from the user's hand due to prolonged repeated use can be excluded.

Lastly, the temperature calculation portion 14 stores the temperature Cd that was corrected as described above as the current temperature in the current temperature area 19 of the storage portion 13 (step S24 in FIG. 8).

The control portion 10 then acquires the current temperature from the current temperature area 19 and corrects the measurement value such as the blood glucose level obtained by the measurement portion 15 using the current temperature (step S6 in FIG. 5) as described above.

As a result, the measurement value can be corrected using temperature information that excludes the influence of heat from the user's hand, thus making it possible to reduce measurement error.

Then, after waiting for 10 seconds (10-second wait) (step S25 in FIG. 8), the procedure returns to step S22 in FIG. 8, and the measurement of the current temperature is started again.

The processing of steps S22 to S25 in FIG. 8 is repeated until the user switches off the power switch 12, and therefore the control portion 10 can always acquire the most recent current temperature from the current temperature area 19 of the storage portion 13.

Furthermore, in the present embodiment, a partition 50 is provided between an accommodating portion for the temperature correction sensor C provided in the grip portion 51a on the one end side and an accommodating portion for the temperature detection sensor D on the other end side as shown in FIG. 9. Accordingly, heat exchange between the one end side and the other end side can be disrupted, and it is possible to reduce the influence that heat from the user's hand that was transmitted to one side has on the other side.

Note that although the present embodiment is configured such that temperature measurement is performed by the temperature correction sensor C and the temperature detection sensor D before the measurement of biological sample information, and the immediately previous temperature information is utilized, a configuration is possible in which temperature measurement is performed by the temperature correction sensor C and the temperature detection sensor D when biological sample information is measured.

The present embodiment was described taking the example of providing the grip portion 51a on only the one end side. In this case, the temperature change detected by the temperature detection sensor D in the end portion on the side opposite to the grip portion 51a (i.e., on the other end side) is smaller. In other words, since it is possible to specify the temperature detection sensor D for which the temperature change is smaller, there is no need to compare the temperature change amounts of the temperature correction sensor C and the temperature detection sensor D.

Note that when the grip portion 51a is provided on the other end side rather than the one end side, the temperature change in the end portion on the one end side is smaller. In this case, when the measurement portion 15 performs measurement, the temperature difference between the first detection temperature Cc detected on the other end side and the second detection temperature Cd detected on the one end side is obtained, and the temperature information from the end portion on the one end side where the temperature change is smaller (i.e., the second detection temperature Cd) is corrected using temperature difference information that corresponds to the temperature difference.

As described above, the present embodiment includes the substantially elongated body case 31 that has the biological sample sensor mounting portion 33 on the one end side, the measurement portion 15 connected to the biological sample sensor mounting portion 33, and the control portion 10 connected to the measurement portion 15. The grip portion 51a is provided on the one end side (or the other end side) of the body case 31, and the temperature detection sensor D is provided inside the body case 31 on the side opposite to the grip portion 51a. Furthermore, the temperature correction sensor C is provided inside the body case 31 corresponding to the grip portion 51a.

Specifically, in the present embodiment, when the measurement portion 15 performs measurement, the temperature difference between the first detection temperature Cd detected with the temperature detection sensor D on the other end side and the second detection temperature Cc detected with the temperature correction sensor C on the one end side is obtained. Then, the temperature information from the temperature detection sensor D provided in the end portion on the other end side where the temperature change is smaller (first detection temperature Cd) is corrected using temperature difference information that corresponds to the temperature difference. If the measurement value obtained by the measurement portion 15 is corrected using this corrected temperature information, the measurement value can be corrected using temperature information that was much less influenced by heat from the user's hand, thus making it possible to suppress measurement error.

As described above, the present invention includes a body case that has a biological sample sensor mounting portion on the one end side, a first temperature sensor provided on the one end side inside the body case, a measurement portion connected to the biological sample sensor mounting portion, and a control portion connected to the measurement portion. Also, in the configuration, a second temperature sensor is provided on the other end side inside the body case. When biological sample information measurement is performed in the measurement portion, the temperature change amounts in the two end portions are compared using the first and second temperature sensors. Furthermore, in this configuration, the measurement value regarding the biological sample information is corrected in the measurement portion using temperature information from either one of the first or second temperature sensors that is provided in the end portion where the temperature change is smaller, thus making it possible to suppress measurement error.

In other words, in the present invention, the first temperature sensor is arranged on the one end side of the body case, and the second temperature sensor is arranged on the other end side. Accordingly, when a user gripping the one end side or the other end side of the body case repeatedly and consecutively carries out measurement multiple times while gripping that portion, heat from the hand is transmitted into the end portion on the gripped side. The detection temperature (temperature information) in that end portion thus changes greatly.

In view of this, in the present invention, the measurement value obtained by the measurement portion is corrected using temperature information from either one of the first or second temperature sensors that is provided in the end portion on the side opposite to the end portion where the temperature change is larger, that is to say, the one provided in the end portion where the temperature change is smaller.

As a result, the measurement value can be corrected using temperature information that was much less influenced by heat from the user's hand, thus making it possible to suppress measurement error.

INDUSTRIAL APPLICABILITY

A biological sample measuring apparatus of the present invention is anticipated to be widely utilized as a biological sample measuring apparatus for measuring biological sample information such as a blood glucose level or a lactic acid level from a biological sample.

The invention claimed is:
1. A biological sample measuring apparatus comprising:
an elongated body case, which is elongated in an elongation direction, including a first end side, a second end side opposed to the first end side in the elongation direction of the elongated body case, and a biological sample sensor mounting portion disposed on the first end side;
a data reader provided on the second end side of the elongated body case,
a display portion provided on the second end side of the elongated body case,
a measurement portion configured to perform a biological sample information measurement, via a sensor mounted on the biological sample sensor mounting portion, on a biological sample fluid extracted from a patient and produce a measurement value indicative of an amount of a substance in the biological sample fluid according to the biological sample information measurement;
a grip portion provided on the first end side on an underside portion of the elongated body case and encompassing the biological sample sensor mounting portion;
a temperature detection sensor provided on the second end side in the elongated body case, the temperature detection sensor configured to detect a first temperature;
a temperature correction sensor provided on the first end side in the grip portion, the temperature correction sensor configured to detect a second temperature;
a temperature calculation portion electrically connected to the temperature detection sensor and the temperature correction sensor, and configured to calculate a temperature difference between the first and the second temperature;
a storage portion including a grip temperature correction table configured to store the temperature difference for each of a plurality of grip times and a corresponding temperature change amount of the temperature detection sensor with respect to each of the stored temperature differences before measurement; and
a control portion configured to obtain one of the stored temperature change amounts which corresponds to an average temperature difference at a time of measurement from the grip temperature correction table and to correct the first temperature based on the obtained temperature change amount, and to correct the measurement value based on a corrected first temperature, wherein:
the average temperature difference is obtained by averaging a plurality of past temperature differences; and
a change of the first temperature is smaller than a change of the second temperature when heat is accumulated inside the grip portion.

2. The biological sample measuring apparatus according to claim 1,
wherein the storage portion is configured to record a correction amount corresponding with the temperature difference.

3. The biological sample measuring apparatus according to claim 1, wherein:
the elongated body case further includes a first accommodating portion for the temperature detection sensor, a second accommodating portion for the temperature correction sensor, and a partition; and
the partition separates the first accommodating portion from the second accommodating portion.

4. The biological sample measuring apparatus according to claim 1, wherein:
the first temperature and the second temperature are measured by the temperature detection sensor and the temperature correction sensor before the biological sample information measurement is performed by the measurement portion.

5. The biological sample measuring apparatus according to claim 1, wherein:
the first temperature and the second temperature are measured by the temperature detection sensor and the temperature correction sensor when the biological sample information measurement is performed by the measurement portion.

6. A biological sample measuring method, for use with an apparatus having:
an elongated body case, which is elongated in an elongation direction, including a first end side, a second end side opposed to the first end side in the elongation direction of the elongated body case, a biological sample sensor mounting portion provided on the first end side, and a grip portion provided on the first end side on an underside portion of the elongated body case and encompassing the biological sample sensor mounting portion;
a data reader provided on the second end side of the elongated body case;
a display provided on the second end side of the elongated body case;
a temperature detection sensor provided on the second end side of the elongated body case and detecting a first temperature;
a temperature correction sensor provided on the first end side in the grip portion and detecting a second temperature; and
a storage portion including a grip temperature correction table configured to store a temperature difference between the first and second temperature for each of a plurality of grip times and a corresponding temperature change amount of the temperature detection sensor with respect to each of the stored temperature differences before measurement,
said method comprising:
measuring the first temperature via the temperature detection sensor;
measuring the second temperature via the temperature correction sensor;
performing a biological sample information measurement, via a sensor mounted on the biological sample sensor mounting portion, on a biological sample substance extracted from a patient and producing a measurement value indicative of the biological sample information measurement;
calculating an average temperature difference by averaging a plurality of past temperature differences; and
obtaining one of the stored temperature change amounts which corresponds to the average temperature difference at a time of measurement from the grip temperature correction table and correcting the first temperature based on the obtained temperature change amount and correcting the measurement value based on a corrected first temperature, wherein a change of the first temperature is smaller than a change of the second temperature when heat is accumulated inside the grip portion.

* * * * *